United States Patent [19]
Eichenberger et al.

[11] Patent Number: 6,120,956
[45] Date of Patent: Sep. 19, 2000

[54] YELLOW PTERIDINE HAVING A HUE-ANGLE OF AT LEAST 98

[75] Inventors: Thomas Eichenberger, Basel; Mathias Düggeli, Fribourg; Max Hügin, Rünenberg, all of Switzerland

[73] Assignee: Ciba Specialty Chemicals Corporation, Tarrytown, N.Y.

[21] Appl. No.: 09/294,482

[22] Filed: Apr. 20, 1999

[30] Foreign Application Priority Data

Apr. 24, 1998 [CH] Switzerland ............... 0938/98

[51] Int. Cl.[7] ............ C08K 5/3462; C07D 487/14; C09B 17/00
[52] U.S. Cl. .............. 430/106; 106/498; 524/100
[58] Field of Search ............ 430/44, 106; 544/300; 524/100; 106/498

[56] References Cited

U.S. PATENT DOCUMENTS 5,525,152  6/1996  Roschger et al. ............ 106/498

FOREIGN PATENT DOCUMENTS 0 761 770   3/1997  European Pat. Off. .
98/05718    2/1998  WIPO .
98/18866    5/1998  WIPO .

OTHER PUBLICATIONS

JACS, vol. 77, (1955), pp. 2243–2248.

*Primary Examiner*—John Goodrow
*Attorney, Agent, or Firm*—David R. Crichton

[57] ABSTRACT

The 2,4,5,7-tetraaminopyrimido[5,4-g]pteridine

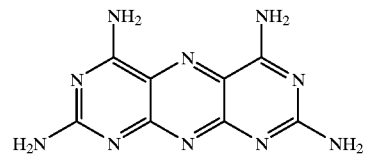

I characterized by a hue-angle h of not less than 98, processes for preparing the pteridine I of the invention, novel, insoluble 2,4,5,7-tetraaminopyrimido[5,4-g]pteridine salts, their preparation and the use of the pteridines of the invention.

23 Claims, No Drawings

YELLOW PTERIDINE HAVING A HUE-ANGLE OF AT LEAST 98

The present invention relates to 2,4,5,7-tetraaminopyrimido[5,4-g]pteridine of the formula I

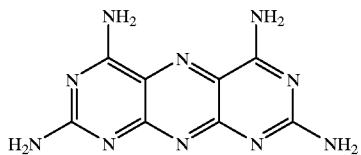

characterized by a hue-angle h of not less than 98 in the L*C*h system of the Commission Internationale de l'Eclairage.

The present invention further relates to processes for preparing the pteridine I of the invention, insoluble pteridine salts II, a sulfamic acid salt of pteridine I, preparation thereof and the use of these pteridines.

JACS 77 (1955) 2243–2248 describes the preparation of a yellow pteridine of the formula I, but it has a hue-angle h of not greater than 88 and is reddish yellow. Moreover, the brilliance of the hue does not meet present-day requirements.

It is an object of the present invention to provide a greenish yellow pteridine of the formula I having a hue-angle of not less than 98. The product shall further have very good fastnesses, a high colour strength and improved brilliance.

This object is achieved by the pteridine I defined at the beginning.

The present invention also provides processes for its preparation, insoluble pteridine salts II, especially a sulfamic acid salt of pteridine 1, preparation thereof and the use of these pteridines.

The pteridine I of the invention has a hue-angle h of not less than 98; the hue-angle is preferably within the range from 98 to 103. The present invention employs the definition of hue-angle which is based on the L*C*h system of the Commission Internationale de l'Eclairage (CIE) (DIN 5033 Part 3; DIN 6174). The L*C*h system correlates with the CIE's 1976 L*a*b* colour space (hereinafter referred to as "CIELab" or "ClELab system") as follows:

the lightness L*—which measures the luminance—is identical in both systems, C* is the chroma and is linked to a* and b* by the following relation:

$$\text{chroma } C^* = \sqrt{(a^*)^2 + (b^*)^2}$$

h is the hue-angle and is linked to a* and b* by the following relation:

$$\text{hue-angle } h_{ab} = tg^{-1}(b^*/a^*)$$

a* describes the green-red axis and b* the yellow-blue axis.

The hue-angle h is preferably determined on a film of a varnish comprising the pteridine I on an aluminium foil. The varnish used is preferably a cured mixture of an alkyd resin and of a melamine-formaldehyde resin, so-called "AM varnish". The pteridine I of the invention has been blended with titanium dioxide (5% by weight of pteridine I, based on the sum total of pteridine I and titanium dioxide) and is present in the AM varnish in a proportion of 4.87% by weight, based on the alkyd resin. The pigmented AM varnish is customarily applied to the aluminium foil together with a mixture of organic solvents as a film 100 μm in thickness, then cured and subsequently calorimetrically measured.

The pteridines I of the invention are generally obtainable by various processes. In a preferred embodiment for preparing the pteridines I of the invention, an insoluble 2,4,5,7-tetraaminopyrimido[5,4-g]pteridine salt II

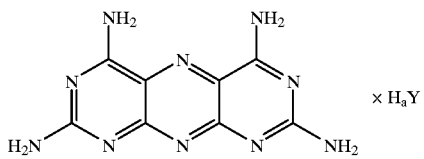

where a is an integer from 1 to 3 and Y is an acid radical, is treated with a base to liberate the pteridine I.

The pteridine salt II can be obtained by reacting 2,4,5,7-tetraaminopyrimido[5,4-g]pteridine with the acid $H_aY$, in which case the acid HaY used is inorganic or organic acid capable of forming an insoluble salt II with 2,4,5,7-tetraaminopyrimido[5,4-g]pteridine.

Examples of useful acids HaY are sulfamic acid and its derivatives, $R_2NSO_3H$, where R is hydrogen and/or $C_1$–$C_4$alkyl such as methyl, ethyl, n-propyl, isopropyl, n-butyl, sec-butyl, isobutyl, tert-butyl, and phosphoric acid, preference being given to sulfamic acid.

Insoluble is to be understood as meaning for the purposes of the present invention such salts II whose solubility at 100° C. does not exceed 1 g in 100 ml of water.

In a particularly preferred embodiment, the salt II is a sulfamic acid salt of the formula III

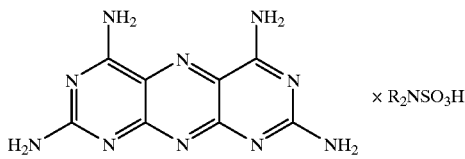

where R is hydrogen or $C_1$–$C_4$alkyl, preferably hydrogen.

The base used for liberating the pteridine I is generally an alkali metal hydroxide such as NaOH or KOH, preferably in the form of an aqueous solution, an alkali metal carbonate or an organic base.

Preference is given to using aqueous alkali metal hydroxide solutions in a concentration within the range from 0.1 to 3, preferably from 0.5 to 2, mol per litre of solution.

The weight ratio of base to pteridine salt II (each based on the corresponding dry weight), especially to pteridine sulfamic acid salt III, is generally within the range from 100:1 to 10:1, preferably within the range from 30:1 to 15:1.

In a preferred embodiment, the base treatment is carried out at elevated temperature, preferably within the range from 60 to 130° C. Particular preference is given to the range from 70 to 85° C.

In the case of temperatures within the range from 95 to 130° C., it can be advisable to employ a superatmospheric reaction pressure, especially in order that the reaction may be carried out in liquid phase.

From observations to date, working within the range from 110 to 130° C. will generally yield an opaque form of the pteridine I. Transparent pteridines I are customarily obtained within the range from 70 to 100° C.; less transparent pteridines are generally obtainable at more than 100° C. to 110° C.

The duration for the base treatment is generally chosen—customarily as a function of the reaction temperature chosen—within the range from 4 to 48, preferably from 12 to 24, hours.

Pteridine I thus liberated can be isolated in a conventional manner, for example by filtration, centrifugation or by decanting. If desired, the pteridine I thus isolated can be additionally washed and dried.

The sulfamic acid salt III is customarily obtained by reacting 2,4,5,7-tetraaminopyrimido[5,4-g]pteridine with $R_2NSO_3H$, preferably where R=H, preferably at elevated temperature.

In a preferred embodiment, the 2,4,5,7-tetraaminopyrimido[5,4-g]pteridine will be the as-synthesized crude product. Particular preference is given to using a crude product obtained by oxidation of 2,4,5,6-tetraaminopyrimidine sulfate with oxygen, preferably with air. More particularly, this oxidation is carried out in aqueous solution at a pH within the range from 6 to 8, preferably in the neutral range. Such a process is extensively described in JACS 77 (1955) 2243–2248 for example. However, the process of the present invention is from observations to date not restricted to this synthesis or to the hue-angle of the 2,4,5,7-tetraaminopyrimido[5,4-g]pteridine to be used.

The molar ratio of 2,4,5,7-tetraaminopyrimido[5,4-g] pteridine to $H_aY$ or $R_2NSO_3H$ is generally within the range from 0.1:1 to 1:1, preferably within the range from 0.5:1 to 0.9:1.

The treatment is preferably carried out within the range from 60 to 100° C., particularly preferably within the range from 75 to 100° C., most preferably within the range from 95 to 100° C.

Furthermore, the treatment is preferably carried out in an aqueous medium. Customarily this means that water is used as solvent, and the amount of sulfamic acid used per litre of water is generally within the range from 1 to 50 g, preferably within the range from 5 to 20 g, particularly preferably within the range from 7 to 15 g, of sulfamic acid.

The reaction pressure chosen will generally be atmospheric pressure for convenience, but it may also be lower or higher, for example within the range from 75 kPa to 5 MPa.

In a preferred embodiment, a mixture of 2,4,5,7-tetraaminopyrimido[5,4-g]pteridine, water and $H_aY$, preferably $R_2NSO_3H$, especially sulfamic acid, is subjected to a treatment with one of the customary high performance dispersing means (for example a high performance stirrer from the ULTRA-TURRAX® range of JANKE-&KUNKEL GmbH&Co, Staufen, Del.) before the reaction mixture is heated. The duration of this dispersing treatment is generally chosen within the range from 1 minute to 30 minutes, preferably within the range from 5 to 15 minutes. The duration may be longer, for example when larger amounts are to be dispersed.

A further embodiment of the present invention relates to insoluble pteridine salts II, preferably sulfamic acid salts III, especially the salt III where R is hydrogen.

A further embodiment of the present invention further provides a process for preparing the insoluble pteridine salts II, especially the sulfamic acid salts III, wherein 2,4,5,7-tetraaminopyrimido[5,4-g]pteridine is treated with an acid $H_aY$, especially $R_2NSO_3H$, particularly preferably sulfamic acid, preferably according to the process already described above.

A further embodiment relates to a further process for preparing the novel pteridines I having a hue-angle h of not less than 98, preferably within the range from 98 to 103, by reacting 2,4,5,7-tetraaminopyrimido[5,4-g]pteridine, preferably the as-synthesized crude product, for example as-oxidized 2,4,5,6-tetraaminopyrimidine sulfate, with an acid $H_aY$, especially $R_2NSO_3H$, particularly preferably sulfamic acid, and, if desired after removal of impurities from the reaction mixture, treating the salt II, preferably the salt III, particularly preferably the salt III where R is hydrogen, with a base to liberate the pteridine I of the present invention.

The crude product obtained by oxidation of 2,4,5,6-tetraaminopyrimidine sulfate is preferably removed from the customarily yellowish orange product mixture in a conventional manner, preferably by filtration.

In a particularly preferred embodiment, this removal step, which generally takes the form of a filtration, is preceded by first treating this yellowish orange product mixture with a base such as an alkali metal hydroxide, for example NaOH, preferably in the form of aqueous sodium hydroxide solution, or KOH, preferably in the form of aqueous potassium hydroxide solution, generally at elevated temperature. This base treatment is generally followed by filtering the mixture while it is still at the elevated temperature, and then the filter residue obtained is washed with water and dried, if desired. As well as filtration, it is also possible to use other commonly used separating methods, such as centrifugation or decanting.

The molar ratio of base to pteridine I for the base treatment mentioned is generally within the range from 1:1 to 20:1, preferably within the range from 2:1 to 10:1, particularly preferably within the range from 3:1 to 4:1.

The temperature for the base treatment is customarily chosen within the range from 60 to 100° C., preferably within the range from 90 to 100° C. The duration of the base treatment is customarily chosen between 1 and 10 hours, preferably between 2 and 4 hours.

According to the invention, this is followed by a reaction with an acid $H_aY$, especially $R_2NSO_3H$, particularly preferably sulfamic acid, which is preferably effected according to the method already described, and the process parameters mentioned there are preferably also employed here.

According to the invention, the pteridine I having a hue-angle h of not less than 98, is then liberated, if desired after removal of impurities, by subsequent treatment of the salt II, especially of the salt III, particularly preferably of the salt II, where R is hydrogen, with a base.

A further preferred embodiment relates to a further process for preparing the pteridine salt II, preferably the sulfamic acid salt III, especially the salt III where R is hydrogen, by treating a 2,4,5,6-tetraaminopyrimidine salt which is not insoluble under the reaction conditions with oxygen in a solvent and thereafter admixing the mixture with sulfamic acid at elevated temperature.

Not insoluble means in this context that the 2,4,5,6-tetraaminopyrimidine salt has a solubility in the particular solvent chosen which is not less than 0.1% by weight, preferably within the range from 1 to 100% by weight, based on the amount of solvent and salt.

A further, particularly preferred embodiment relates to a further process for preparing the pteridine salt II, preferably the sulfamic acid salt III, particularly preferably the sulfamic acid salt III where R is hydrogen, wherein
  (a) a 2,4,5,6-tetraaminopyrimidine salt which is not insoluble under the reaction conditions is treated with oxygen in a solvent,
  (b) then the reaction mixture obtained is treated with a base and, after the base treatment, the insoluble fractions are removed from the reaction mixture, and (c) thereafter the removed insoluble fractions obtained in step (b) are reacted at elevated temperature with $H_aY$, especially $R_2NSO_3H$, particularly preferably sulfamic acid and preferably the insoluble fractions are removed after the reaction.

In these two embodiments, the 2,4,5,6-tetraaminopyrimidine salt, preferably 2,4,5,6-tetraaminopyrimidine sulfate, which is for example commercially available, is customarily oxidized in a solvent in which the salt is not insoluble, i.e. dissolves completely or at least partially (see above for solubility), under the reaction conditions chosen.

Preference is given to using a polar solvent such as water, dimethyl sulfoxide ("DMSO"), dimethylformamide ("DMF"), dimethylacetamide, water-soluble alcohols such as methanol or ethanol, especially a polar protic solvent such as water, methanol or ethanol, particularly preferably water.

The weight ratio of solvent to 2,4,5,6-tetraaminopyrimidine salt is generally within the range from 50:1 to 1:1, preferably within the range from 15:1 to 5:1.

Furthermore, the oxidation is preferably carried out at a pH which is within the range from 5 to 9 at the start of the reaction. The pH range can be set using customary methods, for example by addition of a base such as an alkali metal hydroxide, especially sodium hydroxide, preferably in the form of aqueous sodium hydroxide solution. If desired, it is also possible to use known buffers or buffer solutions.

In a particularly preferred embodiment, the oxidation is carried out in an aqueous medium, and the weight ratio of water, inclusive of the water content of the aqueous base, to the 2,4,5,6-tetraaminopyrimidine salt is within the range from 50:1 to 10:1, preferably within the range from 15:1 to 10:1.

The reaction temperature is generally chosen within the range from 15 to 100° C., preferably within the range from 60 to 100, particularly preferably within the range from 80 to 90° C., in which case the reaction pressure generally corresponds to the atmospheric pressure. By raising the pressure it is also possible to use higher temperatures, for example if it is desired to conduct the reaction at above 100° C. in an aqueous medium.

The reaction time for the oxidation is customarily chosen—as a function of the choice of temperature—within the range from 8 to 72, preferably from 24 to 72, hours. Oxygen is generally passed in the form of a gas through the reaction mixture. Pure oxygen can be used or an oxygen-comprising gas mixture such as nitrogen-oxygen mixtures, especially air.

The amount of oxygen passed through the reaction mixture per unit time is generally chosen within the range from 0.1 to 5, preferably from 0.2 to 2, litres/minute*litre of solvent. If air is used, for example, it is preferable to use 1 to 10, preferably 2 to 4, litres/minute*litre of solvent.

The reaction with $H_aY$, especially $R_2NSO_3H$, particularly preferably sulfamic acid, is preferably carried out as already described above.

In the particularly preferred embodiment, the base used in step (b) is generally an alkali metal hydroxide such as NaOH or KOH, especially in the form of their aqueous solutions such as soda lye or potash lye, preferably aqueous sodium hydroxide solution. The concentration of the aqueous alkali metal hydroxide solution used is generally within the range from 10 to 50%, preferably within the range from 30 to 35%, by weight. The molar ratio of base to pyrimidine salt chosen is generally within the range from 0.5:1 to 10:1, preferably within the range from 1:1 to 5:1, particularly preferably within the range from 1.5:1 to 2:1.

The temperature for this base treatment is customarily within the range from 60 to 100° C., preferably within the range from 90 to 100° C. It is also possible to use a temperature of more than 100° C. without compromising the success of the process of the invention. At temperatures above 100° C. it can be advisable, especially if the base treatment is carried out in the customarily preferred aqueous medium, to raise the pressure appropriately in order that the reaction may be carried out in liquid phase.

The duration chosen for the base treatment, generally as a function of the choice of reaction temperature, is customarily within the range from 1 hour to 10 hours, preferably from 2 to 4 hours.

According to the invention, the 2,4,5,7-tetraaminopyrimido[5,4-g]pteridine obtained in step (b) is isolated in a conventional manner, for example by filtration, decanting or centrifugation, preferably by filtration. The reaction with $H_aY$, especially $R_2NSO_3H$, particularly preferably sulfamic acid, is preferably effected as already described above.

According to the invention, the salt II, especially the sulfamic acid salt IIl, particularly preferably the salt III where R is hydrogen, obtained in step (c) is removed in a conventional manner. This can be accomplished for example by filtration, centrifugation or decanting, preferably by filtration. The residue obtained may optionally be subsequently washed with a suitable liquid to remove further impurities and thereafter if desired dried.

Preferred wash liquids are polar solvents which have little if any solvent power with regard to the salt II, preferably the salt II, for example water.

A further particularly preferred embodiment concerns a process for preparing the pteridines I of the invention by oxidation of a 2,4,5,6-tetraaminopyrimidine salt to 2,4,5,7-tetraaminopyrimido[5,4-g]pteridine, subsequent conversion of the resulting pteridine into a salt, removal of the salt from the reaction mixture and subsequent liberation of the 2,4,5, 7-tetraaminopyrimido[5,4-g]pteridine by treatment of the salt with a base, wherein (a) a 2,4,5,6-tetraaminopyrimidine salt which is not insoluble under the reaction conditions is treated with oxygen in a solvent.

(b) if desired the reaction mixture obtained is then treated with a base and the insoluble fractions are removed from the base-treated reaction mixture, (c) thereafter the removed insoluble fractions are reacted at elevated temperature with an acid $H_ay$, and thereafter the insoluble constituents are removed, and (d) then the removed insoluble constituents are treated with a base.

The acid $H_aY$ used is preferably $R_2NSO_3H$, particularly preferably sulfamic acid (R=hydrogen).

The individual steps of this process are customarily effected according to the process steps specified above.

A further preferred embodiment concerns a further process for preparing the pteridines I of the invention, wherein (a) 2,4,5,7-tetraaminopyrimido[5,4-g]pteridine is if desired treated with a base and then the insoluble constituents are removed from the reaction mixture, (b) 2,4,5,7-tetraaminopyrimido[5,4-g]pteridine which has been treated with a base according to (a) or is untreated is exposed at elevated temperature to a glacial acetic acid treatment, thereafter the insoluble fractions are removed from the reaction mixture and washed, (c) then the removed and washed insoluble fractions are treated with a base at elevated temperature, then the insoluble fractions are removed and washed, and (d) the fractions removed and washed in step (c) are treated with glacial acetic acid at elevated temperature, then the insoluble fractions are removed, washed and, if desired, dried.

Preferably, the 2,4,5,7-tetraaminopyrimido[5,4-g] pteridine used is a crude product obtained by oxidation of a 2,4,5,6-tetraaminopyrimidine salt.

The base treatment of step (a) is preferably carried out according to the process already described above.

The glacial acetic acid treatment in steps (b) and (d) is generally effected by admixing the respectively base-treated 2,4,5,7-tetraaminopyrimido[5,4-g]pteridine with glacial acetic acid using 10 to 50, preferably 20 to 30, l of glacial acetic acid per kg of 2,4,5,7-tetraamino-pyrimido[5,4-g] pteridine (based on dry pteridine). The glacial acetic acid mixture obtained is preferably stirred with a high performance stirrer for a period which is generally within the range from 1 minute to 30 minutes. Thereafter, the invention provides that the glacial acetic acid mixture be heated to a temperature within the range from 70 to 150° C., preferably within the range from 100 to 120° C., for a period which is generally within the range from 1 to 10, preferably 3 to 6, hours. The invention subsequently provides that the insoluble constituents be removed, preferably while still in the hot state, for example by filtration, centrifugation or decanting, preferably by filtration, and washed, preferably initially with glacial acetic acid and then with water, particularly preferably with water having a temperature within the range from 30 to 80° C., most preferably within the range from 45 to 70° C. The wash with water is preferably continued until the wash liquor is pH-neutral. If desired, especially after step (d), the washed fractions are dried.

The base treatment in step (c) is customarily effected by admixing the fractions obtained from step (b) with a base, using in general from 10 to 100 l of an aqueous basic solution per kg of fractions (based on the dry weight). The aqueous basic solution used is preferably an aqueous alkali metal hydroxide solution such as soda lye or potash lye, particularly preferably soda lye. The base is customarily used in an amount within the range from 0.1 mol to 2.5 mol per litre of aqueous solution. The pH chosen is generally within the range of not less than 7, preferably within the range from 7 to 14.

In a preferred embodiment, the basic mixture thus obtained is stirred with a high performance stirrer for a period which generally ranges from 1 minute to 30 minutes. Thereafter the basic mixture is heated to a temperature within the range from 70 to 150° C., preferably within the range from 85 to 100° C., for a period which generally ranges from 0.5 to 5, preferably from 1 to 3, hours. The invention then provides that the insoluble constituents be removed, preferably while still in the hot state, for example by filtration, centrifugation or decanting, preferably by filtration, and washed, preferably initially with the same alkali metal hydroxide solution and then with water, particularly preferably with water having a temperature within the range from 30 to 80° C., most preferably within the range from 45 to 65° C., and the washed fractions are dried if desired.

In a further preferred embodiment, the glacial acetic acid/base/glacial acetic acid variant just described is practised not on 2,4,5,7-tetraaminopyrimido[5,4-g]pteridine but on 2,4,5,6-tetraaminopyrimidine which is preferably first converted into 2,4,5,7-tetraaminopyrimido[5,4-g]pteridine according to one of the processes described above and then used as described under (a) to (d).

The present invention further relates to a further process for preparing the pteridine I of the present invention, which comprises reacting 2,4,6-triaminopyrimidine with diacetylated 2,4,6- triamino-5-nitrosopyrimidine ("diacetyl compound").

The preparation of the blue diacetyl compound (which may also be a mixture of different isomers) having the chemical molecular formula $C_8H_{10}N_6O_3$ is customarily effected by reacting 2,4,6-triamino-5-nitrosopyrimidine with a mixture of acetic anhydride and acetic acid and is described in J.Org.Chem. (1963) 1197–1202, so nothing more needs to be said about that.

The molar ratio of diacetyl compound to 2,4,6-triaminopyrimidine chosen is preferably within the range from 0.5:1 to 2:1, preferably within the range from 0.9:1 to 1.1:1.

The reaction temperature is preferably elevated, particularly preferably within the range from 70 to 125° C.

It is further preferable to conduct the reaction with the diacetyl compound to form the pteridine I in an aqueous basic medium, especially at a pH within the range from 7.5 to 9. After a reaction time of customarily a few hours, preferably within the range from 2 to 50 hours, particularly preferably within the range from 10 to 30 hours, the pH of the reaction mixture is generally shifted by further addition of base, preferably aqueous base, into the strongly basic region, preferably to a pH of not less than 10, particularly preferably to a pH within the range from 12 to 14, and the reaction mixture is then stirred for another 1 to 20 hours, preferably 3 to 10 hours.

In this variant, the preferred solvent is water and the pH is set by adding a customary water-soluble base such as an alkali metal hydroxide, especially sodium hydroxide or potassium hydroxide. The amount of solvent chosen is generally within the range from 5 to 100, preferably from 20 to 50, l per kg of 2,4,6-triaminopyrimidine.

In general, the pteridine I is removed from the reaction mixture by customary measures such as filtration, centrifugation or decanting, preferably filtration, particularly preferably filtration while still hot, i.e. at the reaction temperature chosen, and the residue obtained is washed with water, preferably until the wash liquor is pH-neutral. If desired, the pteridine I obtained can be dried in a conventional manner.

The pteridine I of the present invention is preferably used as a colourant, especially as a pigment, according to methods which are each generally known per se.

The pteridine I is particularly useful for colouring macromolecular organic materials. The pteridine I is further useful for preparing toners and printing inks for various applications such as gravure/flexographic printing, sheeffed offset printing and metal decorating as well as for color filters.

For gravure/flexographic printing it is customary to dilute a printing ink concentrate with a solvent (water and/or an organic solvent) to prepare a printing ink which can then be used in accordance with methods known per se.

The printing ink concentrate is generally prepared by mixing the pteridine I with a clear varnish, the clear varnish having been prepared for example from nitrocellulose, ethanol and other customary additives.

In a preferred embodiment, the printing ink concentrate includes the pteridine I in an amount within the range from 15 to 40% by weight, based on the concentrate. And the amount of pteridine I in the printing ink is generally chosen to be within the range from 10 to 20% by weight, based on the printing ink, depending on the desired application.

When the pteridine I is used in sheetfed offset printing and metal decorating, the pteridine I is used in an amount which is generally within the range from 15 to 30%, preferably 20 to 25%, by weight of pteridine I, based on the pigmented printing ink.

The macromolecular organic materials to be coloured according to this invention can be of natural or synthetic origin. They can be for example natural resins or drying oils, rubber or casein or modified natural substances, such as chlororubber, oil-modified alkyd resins, viscose, cellulose ethers or esters, such as cellulose acetate, cellulose propionate, cellulose acetate butyrate or nitrocellulose, but especially wholly synthetic organic polymers (thermosets and thermoplastics) as obtained by addition polymerization, polycondensation or polyaddition. Exemplary addition polymerization resins are polyolefins such as polyethylene, polypropylene or polyisobutylene, substituted polyolefins such as polymers of vinyl chloride, vinyl acetate, styrene, acrylonitrile, acrylic and/or methacrylic esters or butadiene, and also copolymers of the monomers mentioned, especially ABS or EVA.

Exemplary polyaddition resins and polycondensation resins are the condensation products of formaldehyde with phenols, known as phenolics, and the condensation products of formaldehyde with urea, thiourea and melamine, known as aminoplasts, the polyesters used as surface-coating resins, including both saturated polyesters, e.g. alkyd resins, and unsaturated polyesters, for example maleate resins, also the linear polyesters and polyamides or silicones.

The macromolecular compounds mentioned can be present individually or in mixtures, as plastically deformable materials or melts, which can optionally be spun into fibres.

They can also be present in the form of their monomers or in the polymerized state in dissolved form as film-formers or binders for paints or printing inks, for example, linseed oil varnish, nitrocellulose, alkyd resins, melamine resins, urea-formaldehyde resins or acrylic resins.

The macromolecular organic substances are pigmented with the pteridines I of the present invention for example by mixing such a pigment, optionally in the form of masterbatches, into these substrates using roll mills or mixing or grinding apparatus. The pigmented material is subsequently processed in a conventional manner as by calendering, pressing, extruding, coating, casting or injection moulding into the desired ultimate shape. It is frequently desired to incorporate plasticizers into the macromolecular compounds prior to shaping to produce non-rigid mouldings or to reduce their brittleness. Examples of useful plasticizers are esters of phosphoric acid, phthalic acid or sebacic acid. In the process of the present invention, plasticizers can be incorporated into the polymers before or after the pigment dye has been incorporated. It is further possible, for the purpose of achieving different hues, to add to the macromolecular organic substances not only the pteridines of the formula I but also fillers or other colouring ingredients such as white, colour or black pigments and also effect pigments in the particular quantity desired.

To pigment paints and printing inks, the macromolecular organic materials and the pteridines of the formula 1, optionally together with additional substances such as fillers, other pigments, siccatives or plasticizers, are generally finely dispersed or dissolved in an organic and/or aqueous solvent or solvent mixture. This can be accomplished by dispersing or dissolving the individual components by themselves or else more than one together and only then combining all the components.

A further embodiment accordingly provides mass-coloured macromolecular organic material comprising a pteridine of the formula I, i.e. a pteridine having a hue-angle h of not less than 98, the mass-coloured macromolecular organic material comprising (a) 0.05 to 20% by weight, based on the sum total of (a) and (b), of pteridines I, (b) 99.95 to 80% by weight, based on the sum total of (a) and (b), of a macromolecular organic material, and (c) additives, if desired.

A further embodiment accordingly also provides for the use of the pteridines of the formula I for the mass colouration of macromolecular organic material in a conventional manner, for example by mixing the pteridines I and the macromolecular organic material.

The colourations obtained, for example in plastics, fibres, paints or prints, are notable for a greenish yellow hue, very high colour strength, high saturation, good dispersibility and good fastness to overcoating, migration, heat, light and weather. In printing inks especially, the use of the pteridine I results in outstanding transparency and very good gloss being obtained.

EXAMPLES

The colorimetric properties such as hue-angle h etc. are determined on AM varnishes comprising the pteridine I of this invention. The following procedure is adopted:

A mixture consisting of:
60.00 g of an alkyd resin solution (an alkyd resin is a polyester obtained from polyhydric alcohols and polycarboxylic acids), specifically ALKYDAL®F310 SN (BAYER AG), a mixture consisting of:
  alkyd resin, about 60% in Solvent Naphtha 100 (the latter has CAS No. 64742-95-6)
  xylene, 1.2% by weight
  1,2,4-trimethylbenzene, 14.0% by weight
  propylbenzene, 1.6% by weight
  mesitylene (1,3,5-trimethylbenzene), 4.0% by weight
  (weight %ages each based on the mixture)
  ALKYDAL®F310 having a density of about 1.02 g/cm$^3$ at 20° C., a viscosity of about 6000 mPa.s at 20° C. and an efflux time (4 mm nozzle, according to DIN53211)of>90s
19.00 g of xylene
2.00 g of 1-butanol
2.00 g of 1-methoxy-2-propanol, and
1.00 g of a silicone oil (BAYSILONE®MA, 1% by weight in xylene, BAYER AG) is intensively mixed for 20 minutes. Then 16.00 g of a melamine-formaldehyde resin solution (CYMEL®327 (methylated melamine-formaldehyde resin), about 90% by weight in isobutanol (about 9% by weight) and formaldehyde (about 0.5% by weight), DYNO-CYTEC K.S., NO; viscosity (23° C.): 5100–16,000 mPa.s according to DIN 53019/ 53214; relative density (23° C.) 1.18 g/cm$^3$ according to ISO 2811) are added to the above mixture and again mixed in intensively. To 34.2 g of the mixture obtained are added 600 mg of pigment according to the invention (corresponds to 4.87% by weight, based on alkyd resin used),
11.4 g of titanium dioxide (BAYERTITAN®R-KB-3, BAYER), (weight ratio of pteridine I to titanium dioxide =5:95)
3.8 g of xylene, and also
200 g of glass beads (diameter 2 mm) and the mixture obtained is ground for 60 minutes with a SKANDEX disperser BA-S 20 (from Lau GmbH, Hemer, Del.) at level 2. Thereafter a film applicator is used to apply the ground mixture as a film 100 µm in (wet-film) thickness to aluminium foil followed by drying at 120° C. for 30 minutes.

The colorimetric measurement (including the determination of the colour strength) is effected by means of a DC 3890 spectrophotometer from Datacolor AG, Dietikon, CH, in accordance with the CIELab system, 10° normal observer, D65 standard illuminant, geometry D/8 (in accordance with DIN 5033), with inclusion of gloss.

Inventive Example 1

To a suspension of 191.92 g of commercial 2,4,5,6-tetraaminopyrimidine sulfate (99.3%), 1 l of deionized water and 1 l of 0.5 N aqueous sodium hydroxide solution are added 50.2 ml of 30% by weight aqueous sodium hydroxide solution at room temperature with stirring. Thereafter the pH is 7. Stirring is continued at room temperature for another 15 minutes, and then an air stream of about 6 l/min is passed through the reaction mixture through a dip tube, while the temperature is raised to 85° C. over 30 minutes (pH then still about 6.5). On attainment of the final temperature, the reaction mixture is stirred for 48 hours while air is passed through it all the time.

The yellowish orange reaction mixture obtained is then divided into two portions. One half is filtered off while still hot on a hard paper filter, washed with 1 l of deionized water and dried at 110° C. under reduced pressure to leave 40.95 g of crude product A having the elemental composition 37.58% C, 3.66% H, 53.35% N, (calculated for $C_8H_8N_{10}\cdot 0.7H_2O$: 37.41% C, 3.69% H, 54.54% N)

The other half is admixed with 70 ml of 30% aqueous sodium hydroxide solution and refluxed for three hours at 99° C. with stirring. The mixture is filtered while still hot through a glass fibre/fabric filter and the filter residue is washed with deionized water until the wash liquor is neutral. Drying at 110° C. under reduced pressure leaves 36.64 g of a yellowish orange crude product B having the following elemental composition:

38.15% C, 3.59% H, 54.46% N (calculated for $C_8H_8N_{10}\cdot 0.4H_2O$: 38.21% C, 3.52% H, 55.71% N)

Comparative Example 1 (similar to JACS 77 (1955) 2143-2148)

17.36 g of crude product A are stirred into 2.6 l of glacial acetic acid (100 %), heated to 110° C. and then finally dispersed at a high speed with an ULTRA-TURRAX® stirrer (from JANKE&KUNKEL GmbH&Co, Staufen, Del.) for 10 minutes. The batch is subsequently stirred at 110° C. for a further 90 minutes and filtered hot through a glass fibre/fabric filter. The moist press cake is slurried up in 2.3 l of 0.1 N HCl, heated to the reflux temperature (99° C.) and stirred at that temperature for 30 minutes. Contrary to the literature report, the product does not dissolve completely. The brownish yellow suspension is then filtered hot through a glass fibre/fabric filter. The orange filtrate, after cooling down to room temperature, is adjusted to pH 7 by addition of a 5% by weight aqueous ammonium hydroxide solution, and a yellowish orange precipitate forms. This is followed, while the pH is constantly controlled to 7, by heating to 80° C. and stirring at that temperature for 2 hours. The batch is filtered while still hot through a hard filter paper, and the filter residue is washed with 500 ml of water and dried.

The experiment is repeated with crude product B. Depending on the crude product, the following yields having the respective elemental compositions are found:

From crude product A: 7.68 g of yellowish orange powder.

C: 38.98% H: 3.53% N: 54.74% (calculated for $C_8H_8N_{10}\cdot 0.1H_2O$: C: 39.06% H: 3.36% N: 56.93%

From crude product B: 9.53 g of yellowish orange powder.

C: 38.49% H: 3.59% N: 54.93% (calculated for $C_8H_8N_{10}\cdot 0.3H_2O$: C: 38.49% H: 3.47% N: 56.11%

Inventive Example 2

(a) 18 g of crude product A are slurried up in 1 l of water at room temperature, admixed with 10.84 g of sulfamic acid (99%) and finely dispersed by means of an ULTRA-TURRAX® stirrer for 8 minutes. The batch is heated to the reflux temperature (99° C.) and stirred at that temperature for 45 minutes. The yellow suspension is filtered while still hot and the filter residue is washed neutral with water. The still moist press cake is used directly (see under (b)), a small amount thereof being dried for analytical purposes.

The elemental composition is:

C: 28.82% H: 3.44% N: 44.09% S: 7.79% (calculated for $C_8H_8N_{10}\cdot 0.81H_2NSO_3H\cdot 0.6H_2O$: C: 28.80% H: 3.51% N: 45.38% S: 7.78%)

(b) The sulfamic acid salt of step (a) is added to 1.2 l of 1 N aqueous sodium hydroxide solution and then finely dispersed by means of an ULTRA-TURRAX® stirrer for 8 minutes and thereafter heated to 80°C. The batch is stirred at that temperature for 18 hours, during which the initially yellowish orange suspension takes on a greenish yellow colour. Thereafter it is filtered hot through a glass fibre/fabric filter, and the filter residue is washed neutral with water and dried at 110° C. under reduced pressure.

The elemental composition is

C: 38.27% H: 3.61% N: 55.02% (calc. for $C_8H_8N_{10}\cdot 0.4H_2O$: C: 38.21% H: 3.52% N: 55.71%)

Inventive Example 3

Inventive Example 2 is repeated with 18 g of crude product B instead of crude product A.

The elemental composition of the sulfamic acid salt is:

C: 28.64% H: 3.39% N: 44.80% S: 8.65% (calc. for $C_8H_8N_{10}\cdot 0.9H_2NSO_3H\cdot 0.2H_2O$: C: 28.66% H: 3.34% N: 45.55% S: 8.61%)

The elemental composition of the end product is:

C: 38.45% H: 3.56% N: 54.98% (calc. for $C_8H_8N_{10}\cdot 0.3H_2O$: C: 38.49% H: 3.47% N: 56.11%)

The table below contains the colour coordinates of the products prepared according to the invention, and of comparative examples, after 5:95 incorporation in AM varnish and application to aluminium:

TABLE

| Example | Starting crude product | Method of purification | L* | C* | h | Colour strength |
|---|---|---|---|---|---|---|
| Inv. 3 | B (with NaOH) | invention | 90.56 | 63.54 | 99.23 | 100 |
| Inv. 2 | A (without NaOH) | invention | 89.88 | 61.89 | 98.18 | 97.2 |
| Comp. 1 | B (with NaOH) | prior art | 88.09 | 50.79 | 90.73 | 53.3 |
| Comp. 1 | A (without NaOH) | prior art | 86.72 | 51.98 | 87.43 | 59.8 |

The colour strength of Inventive Example 3 is set at 100 and the other colour strength values are based thereon.

Inventive Example 4

(Preparation of an Opaque Version of Pteridine I by Glacial Acetic Acid/Aqueous Sodium Hydroxide Solution/Glacial Acetic Acid Treatment) 251.14 g of moist press cake of crude product B, prepared similarly to Inventive Example 1 (strength: 30.8% by weight of dry matter), are finely dispersed in 1.7 l of glacial acetic acid (100%) by means of an ULTRA-TURRAX® stirrer for 3 minutes. This is followed by heating to a temperature within the range from 105 to 110° C. and subsequent stirring at that temperature for 4 hours. Thereafter the greenish yellow suspension is filtered while still hot through a glass fibre/hard paper filter, and the filter residue is washed with 300 ml of glacial acetic acid (100%) and with 3.5 l of hot water (about 55° C.). Yield of moist press cake: 208.06 g.

202.61 g of this moist press cake are finely dispersed in 2 l of 1 N aqueous sodium hydroxide solution by means of an ULTRA-TURRAX® stirrer for 3 min, at which point the mixture thus obtained is heated to a temperature within the range from 90 to 95° C. and stirred at that temperature for 2 hours. The greenish yellow suspension is filtered while still hot through a glass fibre/hard paper filter, and the filter residue is washed with 400 ml of 1 N aqueous sodium hydroxide solution and with 2.8 l of hot water (about 55° C.). Yield of moist press cake: 221.22 g.

212.08 g of this moist filter cake are finely dispersed in 1.6 l of glacial acetic acid (100%) by means of an ULTRA-TURRAX® stirrer for 3 min, at which point the mixture thus obtained is heated to a temperature within the range from 105 to 110° C. and stirred at that temperature for 4 hours. It is then filtered whilst hot through a glass fibre/hard paper filter, and the filter residue is washed first with 500 ml of glacial acetic acid and then with 4.8 l of hot water (about 65° C.) until the last wash liquor is neutral (check with pH paper). Drying at 110° C. under reduced pressure leaves 65.6 g of a yellow powder having the elemental composition:

C: 38.74% H: 3.47% N: 55.76% (calc. for $C_8H_8N_{10}.0, 2H_2O$: C: 38.77% H: 3.42% N: 56.52%

After 5:95 incorporation in AM varnish and application to aluminium the following CIELab values are obtained:

L*: 90.88 C*: 52.38 h: 98.45

Inventive Example 5

A green suspension consisting of 2.40 g of a diacetylated 2,4,6-triamino-5-nitrosopyrimidine ($C_8H_{10}N_6O_3$), prepared according to Journal of Organic Chemistry (1963) 1197–1202, especially page 1200 bottom right, 1.28 g of 2,4,6-triaminopyrimidine and 50 ml of deionized water is heated to a temperature within the range from 90 to 95° C. and then stirred at that temperature for 20 hours during which the pH is maintained at about 8 by addition of 1 N aqueous sodium hydroxide solution. Thereafter the pale orange suspension is admixed with 30 ml of 1 N aqueous sodium hydroxide solution, followed after 2 hours by a further 50 ml, while the temperature is maintained at 95° C. The pale yellow suspension is subsequently stirred at that temperature for a further 5 hours and then filtered through a hard filter paper, and the filter residue is washed with water until the wash liquor is neutral (check by means of pH paper). Drying the residue under reduced pressure at 110° C. leaves 0.71 g of a yellow powder having the elemental composition C: 39.18% H: 3.59% N: 53.49% (calc. for $C_8H_8N_{10}.0, 1H_2O$: C: 39.06% H: 3.36% N: 56.93%)

After 5:95 incorporation in AM varnish and application to aluminium the following CIELab values are obtained:

L*: 90.63 C*: 63.61 h: 102.39

Inventive Example 6

(a) Preparation of a clear varnish 20 parts by weight of nitrocellulose (NITROCELLULOSE®A 400, comprising 18% by weight of bis-2-ethylhexyl phthalate ("dioctyl phthalate" or "DOP"), from WOLF WALSRODE AG, DE), 4 parts by weight of a plasticizer (DOP), 56 parts by weight of ethanol, and 20 parts by weight of ethyl acetate are thoroughly mixed.

(b) Preparation of a printing ink

To a dispersion consisting of 15 parts by weight of pteridine I of the invention, 20 parts by weight of the clear varnish of (a), and 25 parts by weight of ethanol (prepared by intensive stirring of the stated ingredients for 30 minutes) are added a further 40 parts by weight of the clear varnish of (a) with intensive stirring for 5 minutes. This is followed by a treatment in a bead mill at 4000 revolutions/minute for 10 minutes.

The colourings obtained with this printing ink possess very high colour strength, high gloss and excellent light and chemical resistance.

What is claimed is:

1. The 2,4,5,7-tetraaminopyrimido[5,4-g]pteridine of the formula I

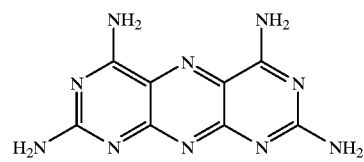

characterized by a hue-angle h of not less than 98 in the L*C*h system of the Commission Internationale de l'Eclairage.

2. A process for preparing the pteridines I according to claim 1, which comprises treating an insoluble 2,4,5,7-tetraaminopyrimido[5,4-g]pteridine salt of the formula I

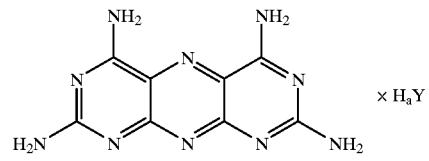

where a is an integer from 1 to 3 and Y is an acid radical, with a base to liberate the pteridine I according to claim 1.

3. A process according to claim 2, wherein $H_aY$ is $R_2NSO_3H$ and R is hydrogen or $C_1$–$C_4$alkyl.

4. The 2,4,5,7-tetraaminopyrimido[5,4-g]pteridine salt of the formula II according to claim 2.

5. A sulfamic acid salt of the formula III

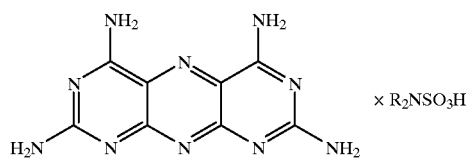

× R₂NSO₃H where R is hydrogen or $C_1$–$C_4$alkyl.

6. A process for preparing the salt II according to claim 2, wherein 2,4,5,7-tetraaminopyrimido[5,4-g]pteridine is reacted with the acid $H_aY$.

7. A process for preparing a 2,4,5,7- tetraaminopyrimido [5,4-g]pteridine of formula I

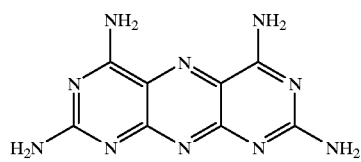

characterized by a hue-angle h of not less than 98 in the L*C*h system of the Commission Internationale de l'Eclairage, wherein 2,4,5,7-tetraamino-pyrimido[5,4-g] pteridine is reacted with the acid $H_aY$, the resulting salt II according to claim 2 removed, and the removed salt II is then treated with a base to liberate the pteridine I of the invention.

8. A process according to claim 7, wherein the 2,4,5,7-tetraaminopyrimido[5,4-g]pteridine used is obtained from the oxidation of 2,4,5,6-tetraaminopyrimidine sulfate.

9. A process according to claim 8, wherein the crude product obtained by oxidation of 2,4,5,6-tetraaminopyrimidine sulfate is removed from the product mixture in a conventional manner prior to further reaction.

10. A process according to claim 9, wherein the product mixture comprising the crude product is first treated with a base at an elevated temperature, then the removal is effected while the base-treated product mixture is still hot, and the removed fractions thus obtained are washed with water and thereafter, if desired, dried.

11. A process for preparing the 2,4,5,7-tetraaminopyrimido[5,4-g]pteridine salt II according to claim 2, wherein a 2,4,5,6-tetraaminopyrimidine salt which is not insoluble under the reaction conditions is treated with oxygen in a solvent and thereafter the mixture is reacted at elevated temperature with the acid $H_aY$, preferably $R_2NSO_3H$.

12. A process for preparing the 2,4,5,7-tetraaminopyrimido[5,4-g]pteridine salt II according to claim 2, wherein
(a) a 2,4,5,6-tetraaminopyrimidine salt which is not insoluble under the reaction conditions is treated with oxygen in a solvent,
(b) then the reaction mixture obtained is treated with a base and, after the base treatment, the insolubles are removed from the reaction mixture, and
(c) thereafter the removed insolubles obtained in step (b) are reacted at elevated temperature with the acid $H_aY$ and preferably after the reaction the insolubles are removed.

13. A process for preparing the pteridines I according to claim 1 by oxidation of a 2,4,5,6- tetraaminopyrimidine salt to 2,4,5,7-tetraaminopyrimido[5,4-g]pteridine, subsequent conversion of the resulting pteridine into a salt, removal of the salt from the reaction mixture and subsequent liberation of the 2,4,5,7-tetraaminopyrimido[5,4-g]pteridine by treatment of the salt with a base, wherein
(a) a 2,4,5,6-tetraaminopyrimidine salt which is not insoluble under the reaction conditions is treated with oxygen in a solvent,
(b) if desired the reaction mixture obtained is then treated with a base and the insoluble fractions are removed from the base-treated reaction mixture,
(c) thereafter the removed insoluble fractions are reacted at elevated temperature with $H_aY$, and thereafter the insoluble constituents are removed, and
(d) the insoluble removed constituents are treated with a base.

14. A process for preparing the pteridines I according to claim 1, wherein
(a) 2,4,5,7-tetraaminopyrimido[5,4-g]pteridine is if desired treated with a base and then the insoluble constituents are removed from the reaction mixture,
(b) 2,4,5,7-tetraaminopyrimido[5,4-g]pteridine which has been treated with a base according to (a) or is untreated is exposed at elevated temperature to a glacial acetic acid treatment, thereafter the insoluble fractions are removed from the reaction mixture and washed,
(c) then the removed and washed insoluble fractions are treated with a base at elevated temperature, then the insoluble fractions are removed and washed, and
(d) the fractions removed and washed in step (c) are treated with glacial acetic acid at elevated temperature, then the insoluble fractions are removed, washed and, if desired, dried.

15. A process for preparing the pteridine I according to claim 1, which comprises reacting 2,4,6-triaminopyrimidine with diacetylated 2,4,6-triamino-5-nitrosopyrimidine.

16. High molecular organic materials comprising a pteridine I according toe claim 1.

17. Toner comprising a pteridine I according to claim 1.

18. Printing ink comprising a pteridine I according to claim 1.

19. Color filter comprising a pteridine I according to claim 1.

20. A process according to claim 2 wherein $H_aY$ is sulfamic acid.

21. A sulfamic acid salt according to claim 5 wherein R is hydrogen.

22. A process according to claim 13 wherein $H_aY$ is $R_2NSO_3H$ and Ri is hydrogen or $C_1$–$C_4$alkyl.

23. A process according to claim 13 wherein $H_aY$ is sulfamic acid.

* * * * *